(12) United States Patent
DiFiore

(10) Patent No.: US 6,808,510 B1
(45) Date of Patent: Oct. 26, 2004

(54) MULTI-LUMEN CATHETER AND TIP CONFIGURATIONS FOR USE THEREWITH

(75) Inventor: Attilio DiFiore, Taylorsville, UT (US)

(73) Assignee: C.R Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/649,680

(22) Filed: Aug. 28, 2000

Related U.S. Application Data

(63) Continuation-in-part of application No. 09/429,857, filed on Oct. 29, 1999, now Pat. No. 6,786,884.

(51) Int. Cl.[7] .................................................. A61M 5/00
(52) U.S. Cl. ........................ 604/171; 604/523; 604/43
(58) Field of Search ............................. 604/27, 35, 40, 604/43–45, 171, 264, 523

(56) References Cited

U.S. PATENT DOCUMENTS

| | | |
|---|---|---|
| 1,696,018 A | 12/1928 | Schellberg |
| 3,595,230 A | 7/1971 | Suyeoka |
| 4,134,402 A | 1/1979 | Mahurkar |
| 4,392,853 A | 7/1983 | Muto |
| D272,651 S | 2/1984 | Mahurkar |
| 4,515,592 A * | 5/1985 | Frankhouser ............... 604/163 |
| 4,547,194 A | 10/1985 | Moorehead |
| 4,551,137 A | 11/1985 | Osborne |
| 4,568,329 A | 2/1986 | Mahurkar |
| 4,583,968 A | 4/1986 | Mahurkar |
| 4,619,643 A | 10/1986 | Bai |
| 4,623,327 A | 11/1986 | Mahurkar |
| 4,634,433 A | 1/1987 | Osborne |
| 4,643,711 A | 2/1987 | Bates |
| 4,692,141 A | 9/1987 | Mahurkar |
| 4,693,257 A * | 9/1987 | Markham ................... 600/565 |
| 4,758,336 A | 7/1988 | Bock et al. |
| 4,770,652 A | 9/1988 | Mahurkar |
| 4,808,155 A | 2/1989 | Mahurkar |
| 4,842,582 A | 6/1989 | Mahurkar |
| 4,892,518 A | 1/1990 | Cupp et al. |
| 4,895,561 A | 1/1990 | Mahurkar |
| 4,913,704 A | 4/1990 | Kurimoto |
| 4,995,865 A | 2/1991 | Gahara et al. |
| 5,092,846 A | 3/1992 | Nishijima et al. |
| 5,106,368 A | 4/1992 | Uldall et al. |
| 5,167,623 A | 12/1992 | Cianci et al. |
| 5,197,951 A | 3/1993 | Mahurkar |
| 5,221,255 A | 6/1993 | Mahurkar et al. |
| 5,221,256 A | 6/1993 | Mahurkar |
| 5,242,398 A | 9/1993 | Knoll et al. |
| 5,250,038 A | 10/1993 | Melker et al. |
| 5,256,150 A | 10/1993 | Quiachon et al. |
| 5,348,536 A | 9/1994 | Young et al. |
| 5,374,245 A | 12/1994 | Mahurkar |
| 5,378,230 A | 1/1995 | Mahurkar |
| 5,395,316 A | 3/1995 | Martin |
| 5,409,461 A | 4/1995 | Steinman |

(List continued on next page.)

FOREIGN PATENT DOCUMENTS

| | | |
|---|---|---|
| CA | 1 150 122 | 7/1983 |
| EP | 0 495 263 A1 | 7/1992 |
| WO | WO 97/17102 | 5/1997 |
| WO | PCT/US01/26849 | 3/2002 |

*Primary Examiner*—Michael J. Hayes
(74) *Attorney, Agent, or Firm*—Morrison & Foerster LLP

(57) ABSTRACT

An improved multi-lumen catheter with tip configurations for the simultaneous injection and withdrawal of fluids. The multi-lumen catheter includes an outer catheter and an inner catheter. The inner catheter is contained within the outer catheter, extends throughout its length and is bisected by a septum to create two parallel lumens. The inner catheter is secured to the outer catheter and may extend beyond the distal end thereof to promote separation between fluids. The multi-lumen catheter can be supplied with a protective sheath to maintain a sterile environment.

27 Claims, 6 Drawing Sheets

U.S. PATENT DOCUMENTS

| | | | |
|---|---|---|---|
| 5,417,665 A | 5/1995 | De La Mata et al. | |
| 5,423,762 A | 6/1995 | Hillstead | |
| 5,431,639 A * | 7/1995 | Shaw | 604/264 |
| 5,451,206 A | 9/1995 | Young | |
| 5,451,216 A | 9/1995 | Quinn | |
| 5,451,233 A | 9/1995 | Yock | |
| 5,472,417 A | 12/1995 | Martin et al. | |
| 5,474,534 A | 12/1995 | Schlitt | |
| 5,486,159 A | 1/1996 | Mahurkar | |
| D367,324 S | 2/1996 | McCarthy et al. | |
| 5,571,093 A | 11/1996 | Cruz et al. | |
| 5,599,305 A | 2/1997 | Hermann et al. | |
| 5,599,322 A | 2/1997 | Quinn | |
| 5,607,462 A | 3/1997 | Imran | |
| 5,624,392 A | 4/1997 | Saab | |
| D381,418 S | 7/1997 | Erskine et al. | |
| D384,411 S | 9/1997 | Musgrave et al. | |
| 5,665,067 A | 9/1997 | Linder et al. | |
| 5,672,158 A | 9/1997 | Okada et al. | |
| 5,676,656 A | 10/1997 | Brimhall | |
| 5,681,288 A | 10/1997 | Schlitt | |
| 5,693,008 A | 12/1997 | Brugger et al. | |
| 5,693,025 A | 12/1997 | Stevens | |
| 5,697,914 A | 12/1997 | Brimhall | |
| 5,722,959 A | 3/1998 | Bierman | |
| 5,727,555 A | 3/1998 | Chait | |
| 5,738,649 A | 4/1998 | Macoviak | |
| 5,755,702 A | 5/1998 | Hillstead et al. | |
| 5,779,681 A | 7/1998 | Bonn | |
| 5,792,094 A | 8/1998 | Stevens et al. | |
| 5,797,869 A | 8/1998 | Martin et al. | |
| 5,807,311 A | 9/1998 | Palestrant | |
| 5,807,318 A | 9/1998 | St. Goar et al. | |
| 5,810,789 A | 9/1998 | Powers et al. | |
| 5,814,016 A | 9/1998 | Valley et al. | |
| 5,843,031 A | 12/1998 | Hermann et al. | |
| 5,961,486 A | 10/1999 | Twardowski et al. | |
| 6,190,371 B1 | 2/2001 | Maginot et al. | |
| 6,508,790 B1 | 1/2003 | Lawrence | |
| 6,592,569 B2 | 7/2003 | Bigus et al. | |

* cited by examiner

MULTI-LUMEN CATHETER AND TIP CONFIGURATIONS FOR USE THEREWITH

CROSS-REFERENCES TO RELATED APPLICATION

This is a continuation-in-part of application Ser. No. 09/429,857, filed Oct. 29, 1999 now U.S. Pat. No. 6,786,884.

BACKGROUND OF THE INVENTION

1. Field of the Invention

The present invention relates generally to medical devices, and more particularly to an improved multi-lumen catheter.

2. Description of Related Art

Multi-lumen catheters are used for a variety of applications where it is necessary to have two or more separate fluid pathways. One such application for a multi-lumen catheter is for use in hemodialysis. During hemodialysis, a dual-lumen catheter can be employed to simultaneously accommodate opposing blood flow. More specifically, one lumen carries blood from a patient to a dialysis machine where it is processed for the removal of toxins, while the opposing lumen returns the purified blood to the patient.

Multi-lumen catheters are well known in the art. Dual lumen catheters, incorporating parallel D-shaped lumen to separate the blood flow and increase the rate of blood flow both into and out of the body, improved upon the use of multiple single lumen catheters. Subsequently, a third circular lumen was introduced to the dual lumen catheters to provide an additional inlet/outlet. Such a catheter can be seen in U.S. Pat. No. 5,797,869 to Martin. In Martin, the third lumen is located in the center of the internal septum, between the two semi-circular lumen. This configuration is intended to give the physician the option of simultaneously injecting a liquid medication during the dialysis procedure, an option not available with a simple dual lumen. However, locating a central lumen between the blood-carrying lumen compromises the reliability of blood flow. Another disadvantage in the catheters of the type described in Martin is that the inlet and outlet openings of the lumen are in close proximity to one another so that toxic blood and purified blood can mix, reducing the efficiency of the process.

SUMMARY OF THE INVENTION

Accordingly, the present invention provides an improved multi-lumen catheter and tip configurations for the simultaneous injection and withdrawal of fluids to and from a patient. The multi-lumen catheter of the present invention is preferably made of polyurethane and is a hollow, cylindrical structure. It includes an outer catheter, generally used for the intake of fluid from the body, and an inner catheter, generally used for injection of fluids into the body. The inner catheter is contained within the outer catheter and extends throughout its length. The hardness of the material used for the inner catheter and outer catheter can be varied, depending on the particular use of the catheter. The material used for the intake lumen should be harder to avoid lumen collapse due to suction, whereas the material used for the outflow lumen should be softer to alleviate trauma to the vein into which the catheter is inserted.

The inner catheter is bisected longitudinally by a septum, which creates two parallel lumens. The shape of each lumen is dependent on the shape of the septum, which can be widely varied. In the case that the inner catheter is split in half, the resulting two lumens are D-shaped. The inner catheter is secured by either the outer catheter's tapered distal end, or a bond, wherein the bond secures the inner catheter to the outer catheter. In a preferred embodiment, the inner catheter extends beyond the distal end of the outer catheter to promote better differentiation between the intake fluid and the outflow fluid. In the case where the multi-lumen catheter is used for hemodialysis, the different lengths of outer and inner catheters help to keep the untreated blood and the purified blood separate. In addition, the two lumens contained within the inner catheter can be of different lengths to maintain fluid separation. The distal end of the two lumens contained within the inner catheter can be varied to improve reliability of fluid flow and avoid vein wall occlusions. For instance, the tips can be beveled, curved, slanted or otherwise altered so that occlusion is less likely. Further, side openings can be cut into either the outer catheter, the inner catheter, or both to improve the reliability of blood flow in the case that one of the lumens becomes occluded. Moreover, a mandrel could be inserted into one of the two lumens within the inner catheter, so that if one of the tubes did become occluded, the mandrel could be removed to provide an open pathway. The lumen could also accompany a guidewire for placement of the catheter.

These and other features and advantages of the present invention will become more apparent to those skilled in the art when taken with reference to the following more detailed description of the preferred embodiments of the invention and the accompanying drawings.

DETAILED DESCRIPTION OF THE INVENTION

Figure 1:
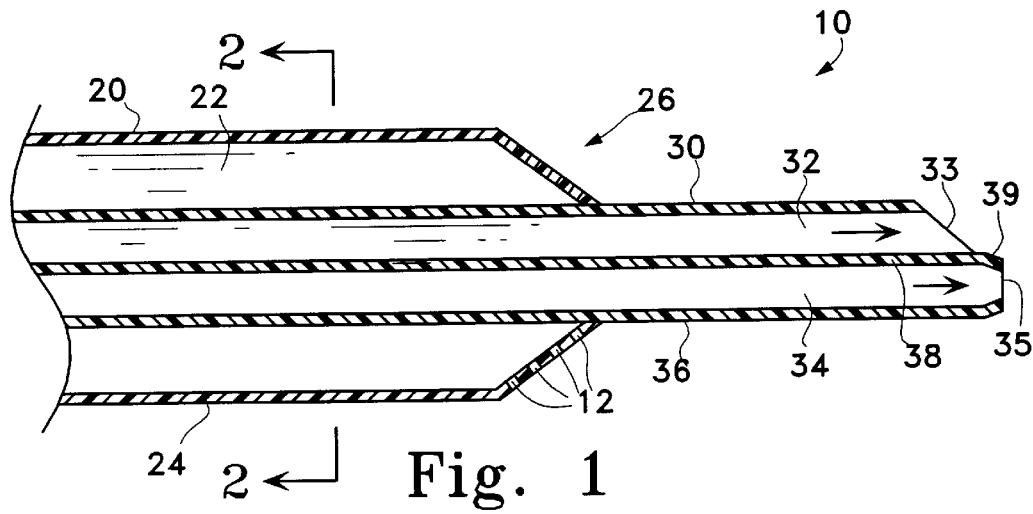
FIG. 1 longitudinal sectional view of an embodiment of the present invention.

The present invention satisfies the need for improved multi-lumen catheters. More particularly, the present invention provides multi-lumen catheters with tip configurations that are efficient and effective in reliably transporting fluids to and from a patient, while avoiding fluid mixing and occlusions. In the detailed description that follows, it should be appreciated that like reference numerals are used to describe like elements illustrated in one or more of the figures.

The multi-lumen catheter of the present invention is a catheter with three or more lumens in which an outer catheter generally surrounds multiple inner lumens. The lumens can be used in any combination for the inflow and outflow of fluids to and from a patient. Further, any one of the lumens can accommodate a mandrel or wire for positioning the multi-lumen catheter. The mandrel or wire can be removed immediately once the catheter is correctly positioned in the patient, or can be left in place, to be removed and used for fluid flow upon the occlusion of one of the other lumens. The multi-lumen catheter can be created by combining an outer catheter with either an inner catheter that has been divided, or with several individual lumens.

Turning now to FIG. 1, one embodiment of the present invention is illustrated. A longitudinal sectional view of a multi-lumen catheter 10 reveals two tubes with three separate passageways. An outer catheter 20 is a hollow, cylindrically-shaped structure that contains a passageway 22, which allows the withdrawal of blood for purification through openings 12 located at or near a distal end 26 (see FIG. 9). The outer catheter 20 is disposed circumferentially around an inner catheter 30, which is also cylindrical, and includes two parallel lumens which are both used for supplying fluid to the patient as indicated by the arrows. In a hemodialysis application, the return fluid is purified blood. Inner catheter 30 includes a first lumen 32 and a second lumen 34, and has a smaller diameter than the outer catheter 20 so that it can be positioned within the outer catheter 20. The inner catheter 30 is secured in the multilumen catheter 10 by the outer catheter 20, which tapers at the distal end 26 from its outer diameter to the outer diameter of the inner catheter 30.

The inner catheter 30 extends beyond the distal end 26 of the outer catheter 20, terminating at a distal end 39. At the distal end 39 of the inner catheter 30, a first outlet 33 of the first lumen 32 is preferably beveled to reduce the chance of vein wall occlusion and other problems associated with blockage of the catheter lumen. A second outlet 35 is preferably blunt, however, to provide a different outlet angle for the fluid. Outlets 33 and 35 can, however, be any configuration known to those skilled in the art. The first and second outlets 33 and 35, while primarily used for the outflow of cleaned blood to the patient, can also be used for other purposes as well. For example, looking at FIG. 1, the edges near the second outlet 35 are tapered inward to better accommodate a guidewire or mandrel. FIG. 1 also shows the second lumen 34 extending slightly beyond the distal end of first lumen 32. The two inner lumen of the present invention can end at the same point or be staggered.

Figure 2:
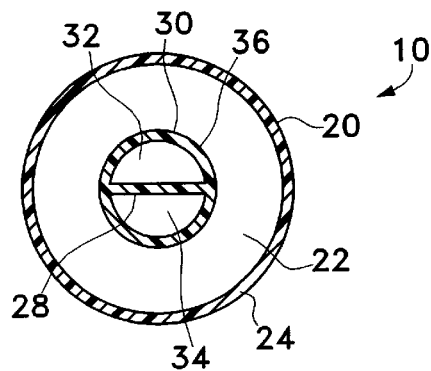
FIG. 2 is a cross-sectional view of FIG. 1 along the line 2—2.

As seen in FIGS. 1 and 2, the first and second lumens 32 and 34 are separated by a septum 38, which extends the length of the multi-lumen catheter 10 from a proximal end, where the individual lumens are joined together, to the distal end 39 of the inner catheter 30. Preferably septum 38 divides the two lumens horizontally into D-shaped cross-sections as shown in FIG. 2, and is preferably made of polyurethane. The wall 24 of the outer catheter 20 and the wall 36 of the inner catheter 30 are also preferably made of polyurethane, but may be made of other recognized materials. The relative hardness of the polyurethane used for the outer wall 24 and the inner wall 36 of the multi-lumen catheter 10 can be varied to achieve a desired result. For example, a harder polyurethane (higher durometer reading) can be used for the outer catheter 20 and a softer polyurethane (lower durometer reading) can be used for the inner catheter 30. By constructing the multi-lumen catheter in this fashion, the outer catheter 20 has greater structural strength to retain its form under the negative pressure created by the withdrawal of blood from the body, while the inner catheter 30 is softer to prevent the risk of vessel wall erosion. Other variations include using different materials for the outer catheter 20 and inner catheter 30, or using a soft tip (low durometer reading) for either the distal end 26 of the outer catheter 20 or the distal end 39 of the inner catheter 30.

Figure 4:
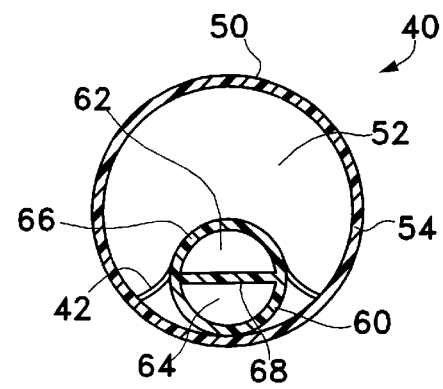
FIG. 4 is a cross-sectional view taken along line 4—4 of FIG. 3.
Figure 3:
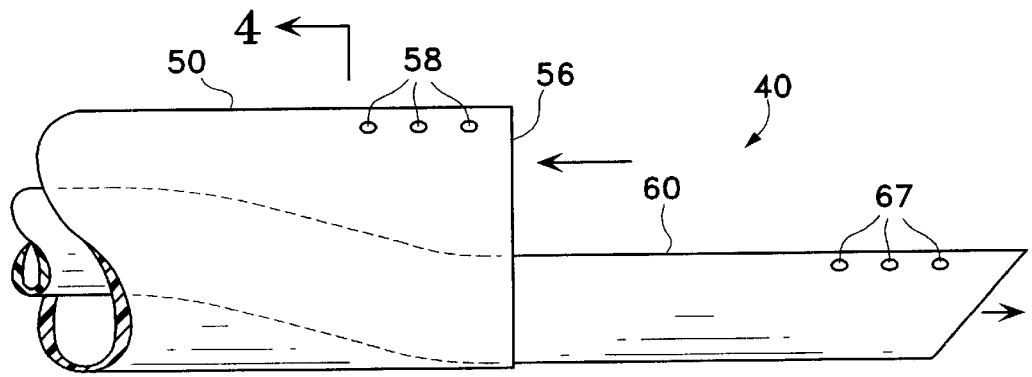
FIG. 3 is a side view of an alternate embodiment of the present invention.

Turning now to FIG. 3, an alternate embodiment of the multi-lumen catheter of the present invention is shown. A side view of a multi-lumen catheter 40 is illustrated, showing an inner catheter 60 extending beyond a distal end 56 of an outer catheter 50. As in the first embodiment, the outer catheter 50 withdraws fluid, while the inner catheter 60 infuses fluid into the body, as indicated by the arrows. The multi-lumen catheter 40 also has three side openings 58 located near the distal end 56 of the outer catheter 50 as well as three side openings 67 located near the distal end 69 of the inner catheter 60. These openings can be varied in size and serve the purpose of ensuring the flow of fluids in the event of a whole or partial occlusion of the inner catheter 60 or the outer catheter 50, as well as improving mixing. The distal end 69 of the inner catheter 60 is beveled to reduce the chance of occlusion from the vein wall. Tapering can be accomplished thermally, using heat and dies, or can be produced by molding. FIG. 4 shows a cross-sectional view of FIG. 3 along line 4—4. The multi-lumen catheter 40 is shown with inner catheter 60 disposed at a point abutting the wall 54 of the outer catheter 50. The inner catheter 60 is maintained in this position by a weld 42 at the distal end 56 of the outer catheter 50, which joins the wall 66 of the inner catheter 60 with the wall 54 of the outer catheter 50 on the interior of the outer catheter 50. The inner catheter 60 is divided horizontally along its entire length by a septum 68, creating two D-shaped passageways, a first lumen 62 and a second lumen 64.

Figure 5:
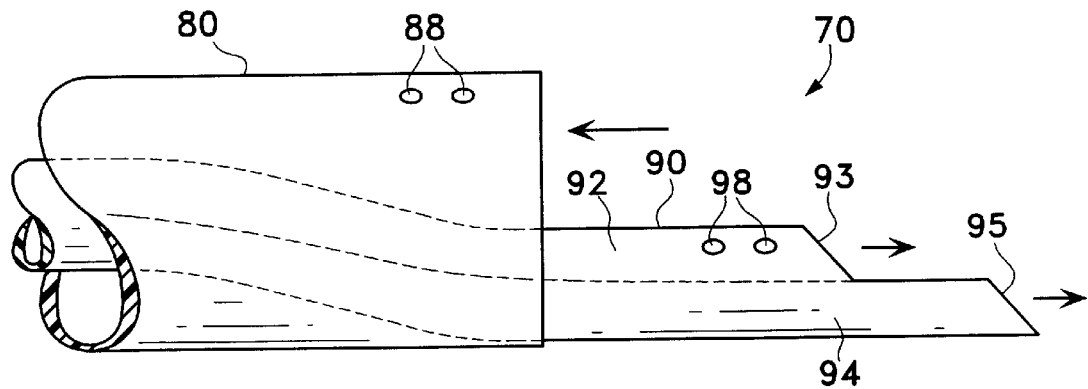
FIG. 5 is a side view of an alternate embodiment of the present invention.

As shown by the dotted lines in FIG. 3, the portion of the inner catheter 60, which remains within the outer catheter 50 preferably has a sharp slope to a concentric position within the outer catheter 50. This is best accomplished, as shown in FIGS. 3 and 5, by stabilizing the inner catheter 60 in a central position within the outer catheter 50. The sharp slope created by such a configuration decreases the likelihood of clotting problems that would occur with a more gradual slope if, for example, the inner catheter were allowed to float free within the outer catheter 50. It should be appreciated that the inner catheter 60 may be bonded to the outer catheter 50 at other locations and in other ways. For instance, a weld could be placed on the exterior of both the outer catheter 50 and the inner catheter 60 at the distal end 56 of the outer catheter 50. Alternatively, the inner catheter 60 could be glued to the outer catheter 50 at any point along the length of the outer catheter 50.

FIG. 5 illustrates a side perspective view of another alternate embodiment of the present invention. A multi-lumen catheter 70 has an outer catheter 80 and an inner catheter 90. As in FIG. 3, both the outer catheter 80 and the inner catheter 90 have side openings 88 and 98, respectively, for improved reliability of lumen patency and mixing of infused fluid. It should be appreciated, however, that either the outer catheter or inner catheter or both could be constructed without openings 88 and 98. The inner catheter 90, as depicted by the dotted line, contains two opposing parallel lumens, a first lumen 92 and a second lumen 94. The first lumen 92 and the second lumen 94 terminate in beveled ends 93 and 95 respectively. The first lumen 92 is longitudinally shorter than the second lumen 94, allowing the multi-lumen catheter 70 to have three stages of flow. This configuration provides more options for mixing and for overcoming occlusion problems that may arise. In an alternate embodiment, the multi-lumen catheter 70 includes a tip portion of the second lumen 94 that is more flexible to reduce the possibility of occlusion, and to lessen the trauma on the vein wall that would occur with a less flexible, harder tip.

Figure 6:
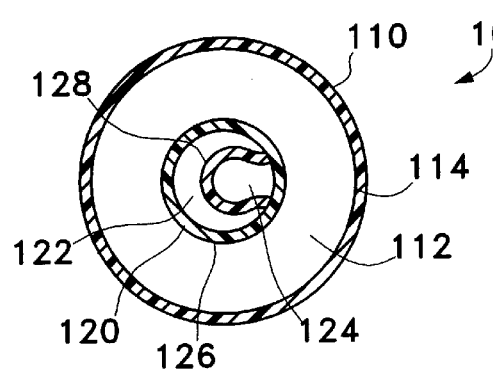
FIG. 6 is cross-sectional view of a one configuration for the inner catheter of the multi-lumen catheter of the present invention.
Figure 7:
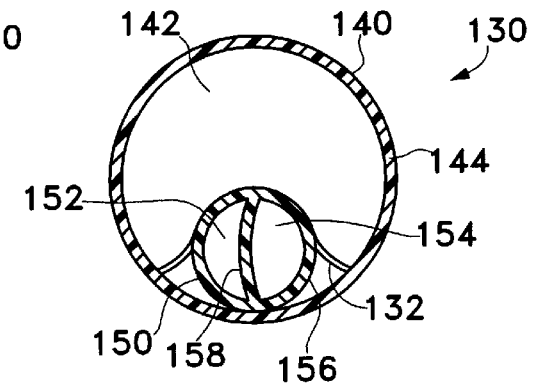
FIG. 7 is a cross-sectional view of an alternate configuration for the inner catheter of the multi-lumen catheter of the present invention.
Figure 8:
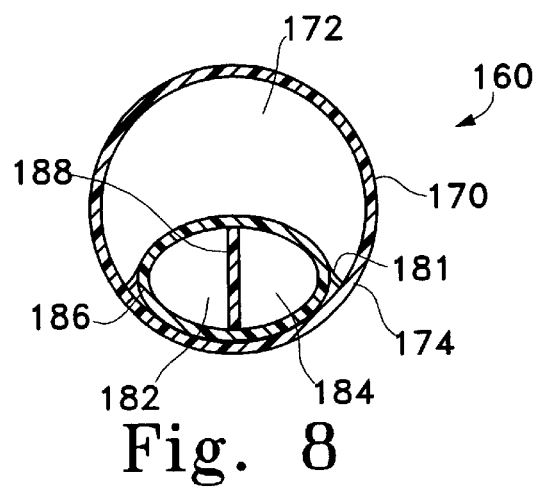
FIG. 8 is a cross-sectional view of another alternate configuration for the inner catheter of the multi-lumen catheter of the present invention.

FIGS. 6–8 show cross-sections of alternate configurations of the inner catheter of the present invention. A multi-lumen catheter 100 of FIG. 6 includes an outer catheter 110 and an inner catheter 120. The outer catheter 110 is a hollow cylindrical structure with a wall 114 and an inner passageway 112. The inner catheter 120 contains a first lumen 122 and a second lumen 124, divided by a C-shaped septum 128. A wall 126 of the inner catheter 120 isolates the liquid flowing through the inner catheter 120 from the liquid flowing through the outer catheter 110. The inner catheter 120 is not bonded to the outer catheter 110 in this configuration, and instead is secured in the catheter 100 by a tapered end of the outer catheter 110, as in FIG. 1. FIG. 7 shows a multi-lumen catheter 130, wherein a wall 156 of an inner catheter 150 is bonded to a wall 144 of an outer catheter 140 by a bond 132. The inner catheter 150 is separated into a first lumen 152 and a second lumen 154 by a septum 158, which bisects the inner catheter 150 essentially vertically, but whose cross-section is bowed in one direction. Thus, a first lumen 152 is crescent shaped, as the bowed shape of the septum 158 bows into the lumen 152. The second lumen 154, as a result, has a cross-sectional area slightly greater than that of a D-shaped cross section as shown in FIG. 4. Making the D-shape of the lumens unequal in size by altering the septa 128 and 158 allows issues of structural integrity and unequal flow requirements to be addressed. It should be appreciated by those skilled in the art that, depending on the functional need of the inner catheter of the present invention, the shape of the septum can be alternately configured. For example, the inner catheter could be divided in such a way that three lumen result from the division. Finally, FIG. 8 shows yet another possible configuration for the cross-section of the inner catheter. A multilumen catheter 160 has an inner catheter 180, which is oval as opposed to the circular examples shown above. The oval wall 186 separates the inner catheter 180 from the fluid flow of the outer catheter 170 and is bonded to the outer catheter 170 by a bond 181. The inner catheter 180 is vertically bisected by a septum 188, producing D-shaped lumens 182 and 184.

Figure 9:
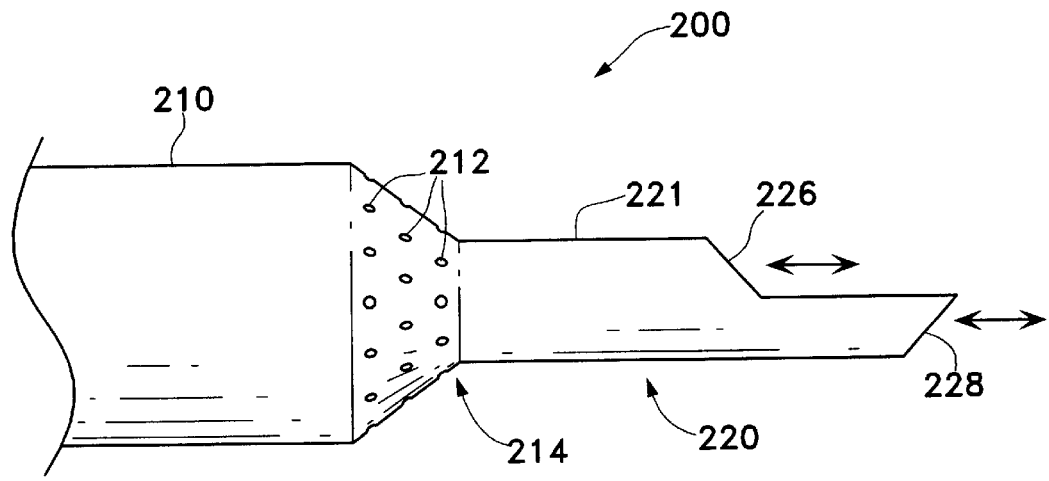
FIG. 9 is a side view of an alternate embodiment of the present invention.
Figure 10:
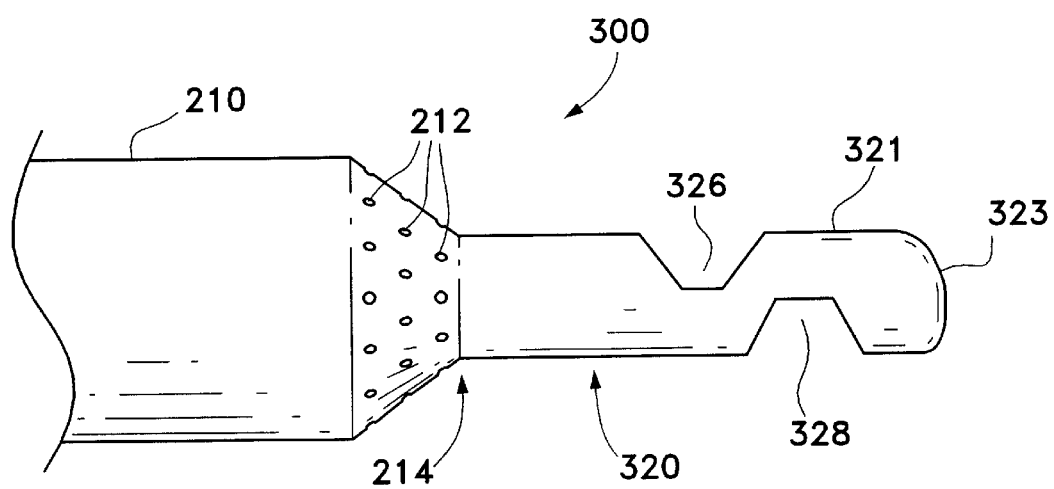
FIG. 10 is a side view of the embodiment in FIG. 9 with a bolus tip configuration.
Figure 11:
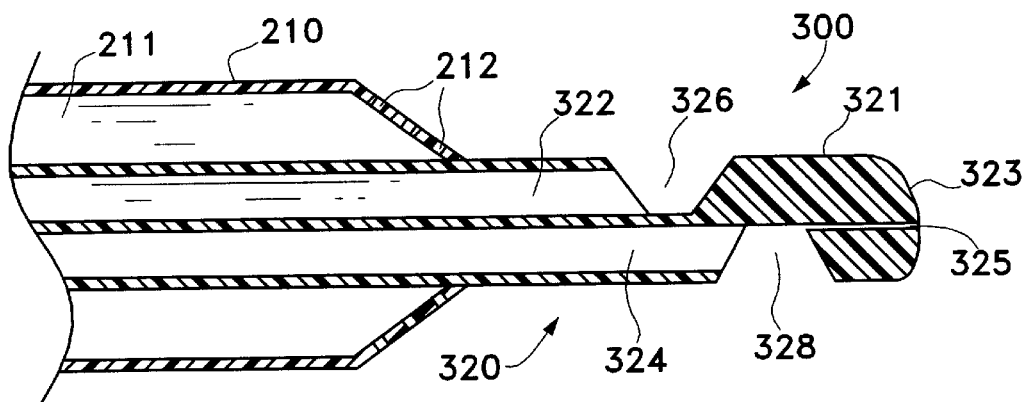
FIG. 11 is a cross-sectional view of the multi-lumen catheter shown in FIG. 10.

FIGS. 9–11 illustrate a preferred embodiment of the present invention. In this embodiment, the inner catheter is held in a central position at the distal end by the narrowing configuration of the outer catheter. Referring to FIG. 9, a multi-lumen catheter 200 includes an outer catheter 210 and an inner catheter 220. The outer catheter 210 has a distal end 214 that narrows to a smaller diameter to accommodate the inner catheter 220. The smaller diameter of the distal end 214 of the outer catheter 210 permits some movement of the inner catheter 220 even though the fit between the outer catheter 210 and the inner catheter 220 at the distal end 214 is sufficiently close to prevent any unwanted drifting of the inner catheter 220. When desired, however, the inner catheter 220 can be moved in a proximal or distal direction to optimize the flow of blood. The distal end 214 of the outer catheter 210 contains side openings 212 which can be varied in number and size and serve the purpose of allowing the withdrawal of blood to a passageway 211 (see FIG. 11) of the outer catheter 210. The inner catheter 220 is divided into a first lumen and a second lumen, and has a tip 221. The first lumen has a beveled opening 226 that is slanted toward the outer catheter 210 as shown in FIG. 9 while the second lumen has a beveled opening 228 that is slanted away from the outer catheter 210. By orienting the bevels in opposite directions, greater separation of blood can be accomplished. As indicated by the arrows, both lumen can support the inflow or outflow of blood.

FIG. 10 illustrates a multi-lumen catheter 300 that includes an outer catheter 210 and an inner catheter 320. The outer catheter 210, described above, accommodates the inner catheter 320, which includes a bolus tip 321 as well as a first lumen 322 and a second lumen 324 (see FIG. 11). The bolus tip 321 is unlike any of the other tips described above in that the openings to the first and second lumens are not located at the distal end of the inner catheter 320. Instead, the first lumen 322 has an opening 326 on one side of the bolus tip 321, wherein a section of the bolus tip 321 has been removed, extending down within the first lumen 322, but short of the second lumen 324 as shown in FIG. 11. Similarly, the second lumen 324 has an opening 328 preferably approximately 180° radially from the opening 326, wherein the opening 328 is horizontally located distal of the opening 326. The bolus tip 321 also includes a rounded nose 323 to prevent unnecessary trauma to the patient's vessel in which it is placed. Variations on the bolus tip 321 can be found in U.S. application Ser. No. 09/429,857, which is incorporated by reference herein.

Referring to the cross-sectional view of multi-lumen catheter 300 in FIG. 11, the tip 321 preferably includes lumen 325 which is added to the tip 321 to accommodate a guidewire. Lumen 325 is shown connecting the second lumen 324 to the end of the nose 323, although it will be appreciated that the guidewire lumen 325 could just as easily be connecting the first lumen 322 to the end of the nose 323.

Figure 12:
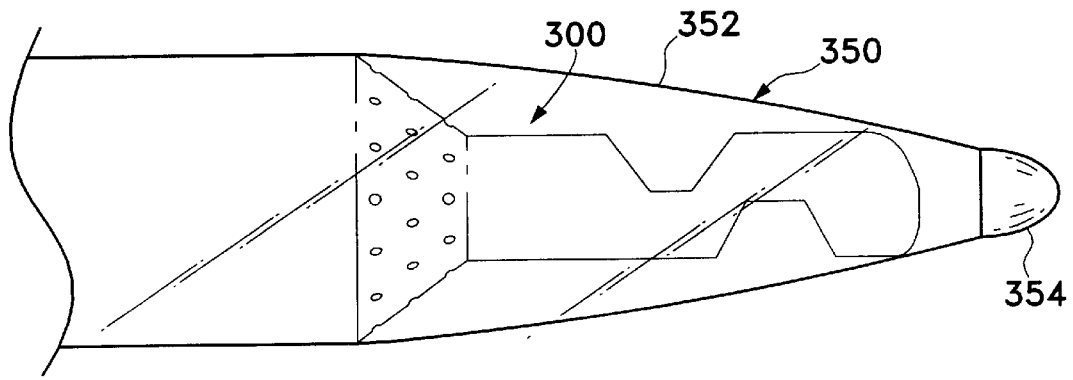
FIG. 12 is a side view of a distal end of the multi-lumen catheter shown in FIG. 10, encased in a protective sheath.
Figure 13:
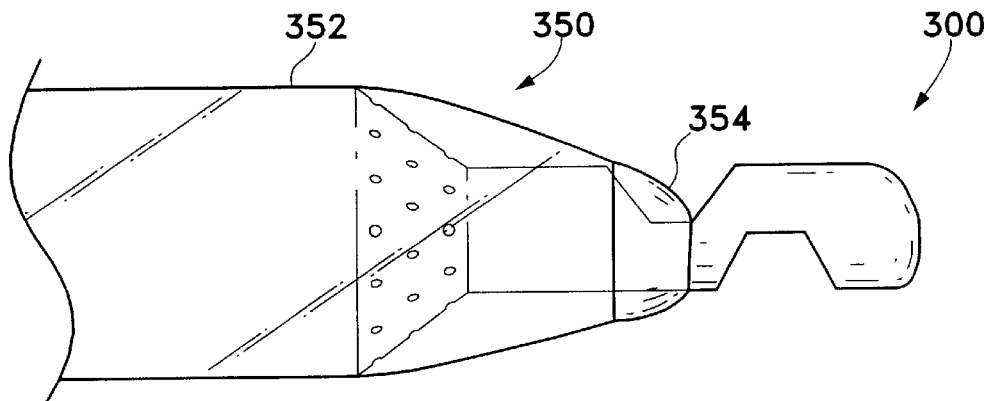
FIG. 13 is a side view of the embodiment in FIG. 12 with the lumens exposed.

FIGS. 12 and 13 illustrate an alternate embodiment of the present invention. The distal end of the multi-lumen catheter 300 is shown encased in a protective sheath 350. The sheath 350, at its distal end, has a main portion 352, which can be tapered and friction fit to the outside of the multi-lumen catheter 300 to snuggly fit around all portions of both the outer catheter 210 and the inner catheter 320, and a self-sealing cap portion 354. FIG. 12 illustrates the catheter 300 when sealed by the sheath 350. The catheter 300 can be introduced to a bodily vessel in this configuration to keep any unwanted fluids or bacteria from entering the lumen. Moreover, the sheath 350 protects the catheter 300 while it is within the bodily vessel and lowers the probability of clotting because it enables the physician to withdraw the inner catheter 320 from the blood stream. Furthermore, if it becomes necessary to flush the lumens of the inner catheter 320, the sheath 350 may permit the physician to use a fluid other than heparin and still maintain patency of the device. Any reduction in the amount of heparin used significantly reduces costs. Another benefit imparted by the use of the protective sheath 350 is that the inner catheter 320 may have a tendency to rest against a vessel wall, depending on the method of placement and the final resting position of the device. By withdrawing the inner catheter 320 within the protective sheath 350, fibrin sheath formation is restricted to the outer catheter 210. In fact, the sliding action of the inner catheter 320 into and out of the outer catheter 210 may actually remove any fibrin sheath formation on the outer catheter 210, or at least function to reduce the clotting effects associated therewith.

FIG. 13 shows the catheter 300 in an open configuration, wherein the sheath 350 seals only a portion of the catheter 300. In this particular case, the flow of fluid into the arterial lumen 322 (see FIG. 11) is partially restricted by the cap portion 354 of the sheath 350 that blocks a portion of the opening 326 (see FIG. 11). Thus, the sheath 350, in addition to providing a sterile environment for the catheter 300, can also be used to regulate the flow of fluids. Of course, due to the highly pliable nature of the cap portion 354, movement is also possible in the opposite direction, in the case that one wants to re-seal the multi-lumen catheter 300. Because the catheter 300 can be sealed and re-sealed by the sheath 350, catheter patency is increased. Further, as mentioned above, the lumens do not need to be heparinized and flushed if they are sealed within the sheath 350. On the other hand, if heparin flushing is required, the sealing aspect of the sheath 350 makes it useful as a heparin lock to prevent clotting and to prevent the toxic release of heparin into the blood.

Figure 14:
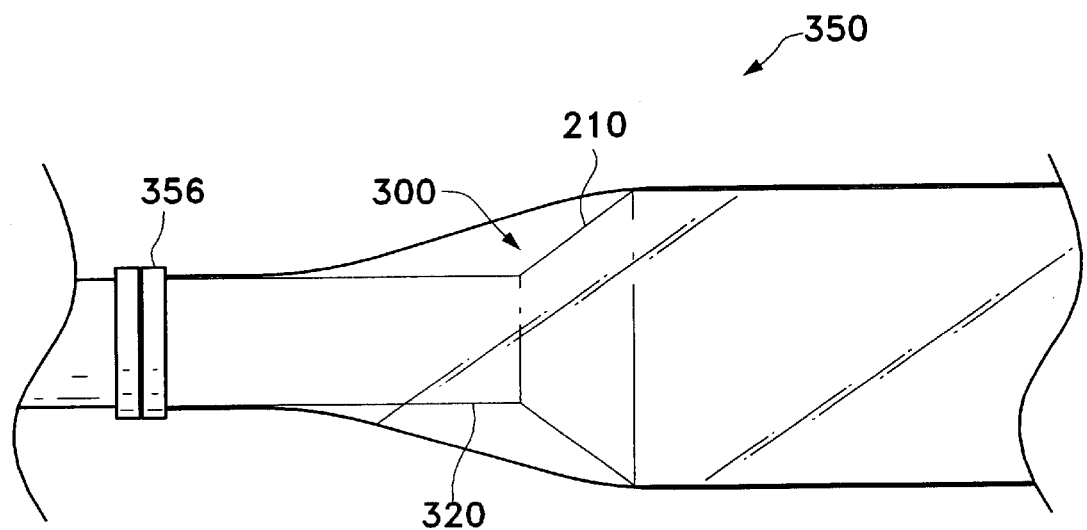
FIG. 14 is a side view of a proximal end of the embodiment in FIG. 12.
Figure 15:
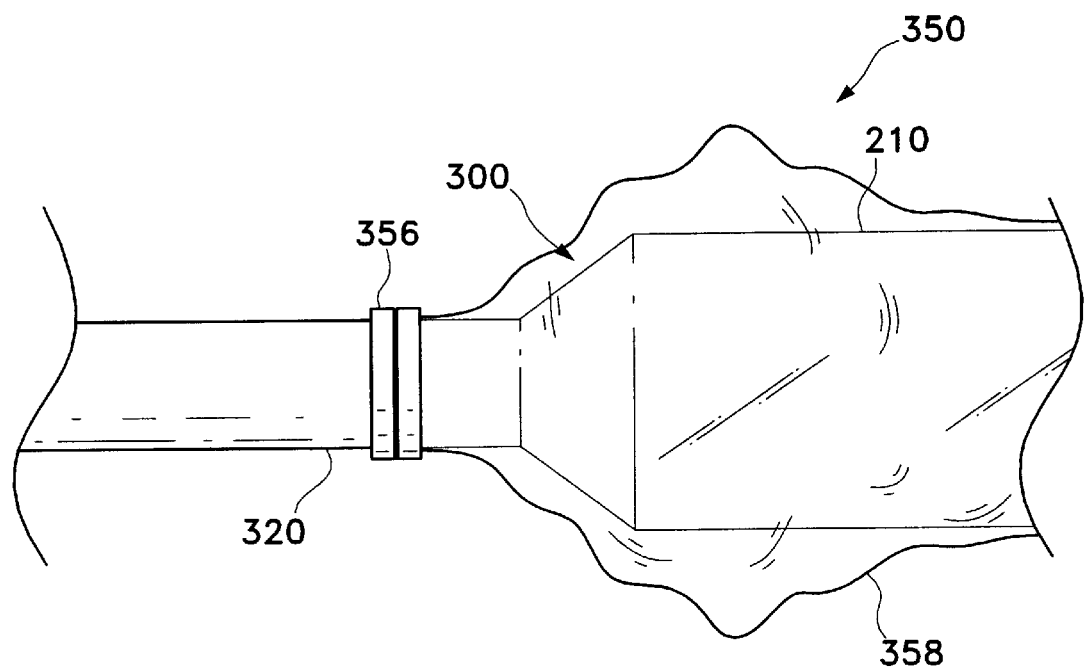
FIG. 15 is a side view of a proximal end of FIG. 13.

FIGS. 14 and 15 show a view of the proximal end of a multi-lumen catheter of the present invention with the sheath 350 over the top of an outer catheter. While not shown in these illustrations, one of the primary benefits of the sheath 350 with the multi-lumen catheters of the present invention is the fact that the sheath 350 can be directly attached to the body. As is well known to those of skill in the art, catheters that are attached to a patient's body for an extended period become fixed in place due to growth and infiltration of the body's cells into the outer wall of the catheter. When the catheter is to be moved in a proximal or distal direction, the portion of the catheter that has become fixed to the body is torn from its bond, potentially causing irritation and discomfort to the patient and acting as a site of potential infection. The use of the sheath 350 overcomes this potential problem because the sheath is composed of soft polyurethane or silicon at the point of attachment and does not move with respect to the body when the catheter is displaced in a proximal or distal direction.

As can be seen in FIG. 14, the sheath 350 is sealingly attached to the inner catheter 320 with a valved O-ring 356. It should be appreciated, however, that the sheath could be attached to the catheter 300 in a variety of different ways. The proximal view of FIG. 14 corresponds to FIG. 12, which shows the catheter 300 in a closed configuration, sealed from outside fluids and possible contaminants. FIG. 15 illustrates what occurs when it is desired to open the catheter 300 to bodily fluids. The inner catheter 320 is pushed from its proximal end, through the self-sealing cap portion 354 until the desired length of the inner catheter 320 is exposed. The O-ring 356 is attached to the inner catheter 320 at its proximal end, creating a sterile environment for the enclosed surface of the catheter 300 when the catheter is manipulated in a proximal and distal direction. When the catheter 300 is exposed to the bodily vessel by pushing the inner catheter 320 in a distal direction so that the nose 323 of the inner catheter 320 extends outside the sheath 350, as can be seen in corresponding FIG. 13, the sterility of catheter 300 is maintained because of the sealed attachment by ring 356. Referring again to FIG. 15, the collapsible portion 358 of the sheath 350 that is located outside of the body and proximal to the attachment point of the body, can be made of a softer polyurethane or silicone than the main portion 352, which can be composed of a higher durometer material. As the inner catheter 320 is advanced in a distal direction, the collapsible portion 358 bunches, but maintains a sterile lock with respect to the inner catheter 320 and the outer catheter 210. This configuration allows the movement of the distal end of catheter 300 in and out of the self-sealing sheath 350, permitting control of fluid flow as well as providing sterility and increased catheter patency.

Figure 16:
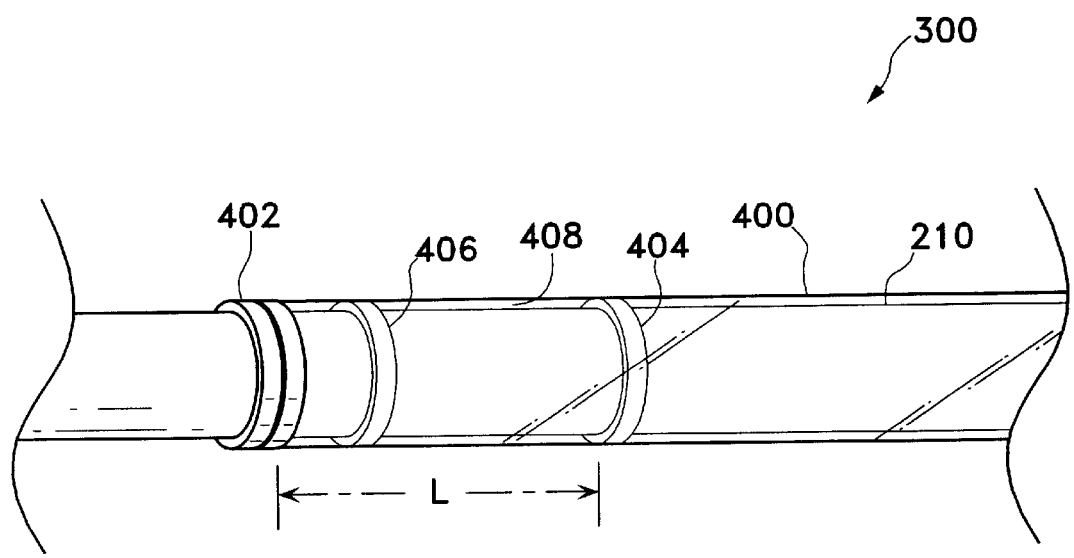
FIG. 16 is a side view of an alternate embodiment of the present invention, showing a protective sheath around the outer catheter.

FIG. 16 illustrates an alternate embodiment of the present invention, showing another means for utilizing a protective sheath. In this embodiment, the multi-lumen catheter 300 is encased in a protective sheath 400, wherein a longitudinal length L of the sheath 400 is filled with an antibacterial agent. The length L is the distance measured from the valved O-ring 402, which seals the sheath 400 at its proximal end, to a stay 404 located distally of the O-ring 402, which prevents distal movement of the outer catheter 210 as will be explained in more detail below. The length L can be any suitable length based on the particular application. Valved O-ring 402 and stay 404 provide a seal around outer catheter 210 over length L, but are not attached to the outer catheter 210 such that the catheter 210 can slide in a proximal or distal direction. However, a damper 406 which is attached to the outer catheter 210 allows travel only over length L. For example, when it is desired to move the outer catheter 210 in either a distal or proximal direction, the stay 404 will prevent the damper 406 from traveling distally and the O-ring 402 will prevent the damper 406 from traveling proximally, thus limiting the respective movement of the outer catheter 210 to which the damper 406 is attached.

Between the O-ring 402 and the stay 404, a sterile cylindrical region 408 is created around the outer catheter 210. Antibacterial agents such as silver-sulfadiazine can be positioned within the region 408 to continually sterilize the outer catheter 210. To this end, the damper 406 can be made of a porous material such as Dacron or a solid material such as neoprene with holes created therein, allowing the passage of fluid through the damper 406 that will permit the antibacterial agent to sterilize all parts of the catheter within the region 408.

Many alterations and modifications may be made by those having ordinary skill in the art without departing from the spirit and scope of the present invention. For example, a multi-lumen catheter has been illustrated with one outer lumen and one inner lumen, separated by a septum to create two smaller inner lumens. It should be apparent, however, that the inventive concepts described above would be equally applicable to a multi-lumen catheter with a larger number of lumen, such as an outer lumen bisected by a septum, each sub-lumen containing an inner lumen, such inner lumen further divided as described above, for a total of six lumen. Moreover, the words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself The definitions of the words or elements of the following claims are, therefore, defined in this specification to include not only the combination of elements which are literally set forth, but all equivalent structure, material or acts for performing substantially the same function in substantially the same way to obtain substantially the same result.

We claim:

1. A multi-lumen catheter apparatus for use in the simultaneous injection of fluids and aspiration of fluids comprising:
   a hollow elongate outer catheter having an outer wall;
   an elongate inner catheter disposed within said outer catheter, defining an annular region therebetween, said inner catheter including an enclosing wall, a septum and a tip, wherein said septurn extends within said enclosing wall of said inner catheter, defining a first and second lumen therein; and
   a protective sheath extendable over the entire length of said inner and outer catheters while said apparatus is within a bodily vessel, wherein said protective sheath includes a sealed region at a proximal end of said apparatus and means for limiting the movement of said apparatus trough said region.

2. The multi-lumen catheter apparatus of claim 1, wherein said protective sheath includes a self-sealing cap at a distal end thereof that permits the passage of the inner catheter therethrough.

3. The multi-lumen catheter apparatus of claim 1, wherein said sealed region contains an antibacterial agent.

4. The multi-lumen catheter apparatus of claim 1, wherein said tip of said inner catheter extends longitudinally beyond a distal end of said outer catheter.

5. The multi-lumen catheter apparatus of claim 1, wherein said septum extends from a proximal end of said inner catheter to said tip.

6. The multi-lumen catheter apparatus of claim 1, wherein said outer catheter tapers from a first diameter to a smaller second diameter at a distal end thereof.

7. The multi-lumen catheter apparatus of claim 6, wherein said outer catheter distal end abuts an outer surface of said inner catheter to substantially center said inner catheter within said outer catheter.

8. The multi-lumen catheter apparatus of claim 1, wherein said tip is formed at an angle, wherein the enclosing wall on a first side of said inner catheter extends longitudinally beyond the enclosing wall on a second side of said inner catheter directly opposite said first side, forming a bevel.

9. The multi-lumen catheter apparatus of claim 1, wherein said tip is angled from said enclosing wall to said septum on one side of said inner catheter, forming a bevel.

10. The multi-lumen catheter apparatus of claim 1, wherein said second lumen of said inner catheter extends longitudinally beyond said first lumen.

11. The multi-lumen catheter apparatus of claim 1, wherein said tip has at first cavity and a second cavity, wherein said first lumen is in fluid communication with said first cavity and said second lumen is in fluid communication with said second cavity.

12. The multi-lumen catheter apparatus of claim 11, further comprising a guidewire lumen, wherein said guidewire lumen extends from said first cavity through said end of said tip.

13. The multi-lumen catheter apparatus of claim 11, further comprising a guidewire lumen, wherein said guidewire lumen extends from said second cavity through said end of said tip.

14. The multi-lumen catheter apparatus of claim 1, wherein said outer wall filer comprises a plurality of openings located near a distal end of said outer catheter, and wherein said annular region is in fluid communication with said openings.

15. The multi-lumen catheter apparatus of claim 1, wherein said enclosing wall further comprises a plurality of openings located near said tip of said inner catheter wherein said first and second lumens are in fluid communication with said openings.

16. A multi-lumen catheter apparatus for use in the simultaneous injection of fluids, and aspiration of fluids comprising:
   a bollow elongate outer catheter having an outer wall, wherein said outer catheter tapers from a first diameter to a smaller second diameter at a distal end thereof;
   an elongate inner catheter disposed within said outer catheter, defining an annular region therebetween, wherein said inner catheter is secured to said outer catheter proximate said distal tapered end of said outer catheter to substantially center said inner catheter within said outer catheter, wherein said inner catheter includes an enclosing wall, a septum and a tip, wherein said tip of said inner catheter extends longitudinally beyond said distal end of said outer catheter, and wherein said septum extends within said enclosing wall of said inner catheter, defining a first and second lumen therein; and
   a protective sheath extendable over the entire length of said inner and outer catheters while said apparatus is within a bodily vessel, wherein said protective sheath includes a sealed region at a proximal end of said apparatus and means for limiting the movement of said apparatus through said region.

17. The multi-lumen catheter apparatus of claim 16, wherein said protective sheath includes a self-sealing cap at a distal end thereof that permits the passage of the inner catheter therethrough.

18. The multi-lumen catheter apparatus of claim 16, wherein said sealed region contains an antibacterial agent.

19. The multi-lumen catheter apparatus of claim 16, wherein said septum extends from a proximal end of said inner catheter to said tip.

20. The multi-lumen catheter apparatus of claim 16, wherein said tip is formed at an angle, wherein the enclosing wall on a first side of said inner catheter extends longitudinally beyond the enclosing wall on a second side of said inner catheter directly opposite said first side, forming a bevel.

21. The multi-lumen catheter apparatus of claim 16, wherein said tip is angled from said enclosing wall to said septum on one side of said inner catheter, forming a bevel.

22. The multilumen catheter apparatus of claim 16, wherein said second lumen of said inner catheter extends longitudinally beyond said first lumen.

23. The multi-lumen catheter apparatus of claim 16, wherein said tip has a first cavity and a second cavity, wherein said first lumen is in fluid communication with said first cavity and said second lumen is in fluid communication with said second cavity.

24. The multi-lumen catheter apparatus of claim 23, further comprising a guidewire lumen, wherein said guidewire lumen extends from said first cavity through said end of said bolus tip.

25. The multi-lumen catheter apparatus of claim 23, fiber comprising a guidewire lumen, wherein said guidewire lumen extends from said second cavity through said end of said tip.

26. The multi-lumen catheter apparatus of claim 16, wherein said outer wall further comprises a plurality of openings located near the distal end of said outer catheter, and wherein said annular region is in fluid communication with said openings.

27. The multi-lumen catheter apparatus of claim 16, wherein said enclosing wall flyer comprises a plurality of openings located near said tip of said inner catheter, and wherein said first and second lumens are in fluid communication with said openings.

* * * * *